United States Patent [19]

Hough et al.

[11] Patent Number: 5,071,747

[45] Date of Patent: Dec. 10, 1991

[54] POROUS POLYMERIC SUPPORT CONTAINING BIOLOGICAL CELLS IN INTERCONNECTED VOIDS

[75] Inventors: David B. Hough; Kevin Hammond, both of Irby; Christine Morris, Upton by Chester; Rober C. Hammond, Radwell, all of England

[73] Assignee: Unilever Patent Holdings B.V., Rotterdam, Netherlands

[21] Appl. No.: 288,149

[22] Filed: Dec. 22, 1988

[30] Foreign Application Priority Data

Dec. 22, 1987 [GB] United Kingdom ............... 8729889

[51] Int. Cl.$^5$ .................. C12P 1/00; C12N 11/08; C12N 11/04; C12N 5/00
[52] U.S. Cl. ............................ 435/41; 435/180; 435/182; 435/240.23
[58] Field of Search ............... 435/41, 174, 176, 177, 435/180, 182, 240.23

[56] References Cited

U.S. PATENT DOCUMENTS

| | | | |
|---|---|---|---|
| 4,149,936 | 4/1979 | Messing et al. | 435/176 |
| 4,153,510 | 5/1979 | Messing et al. | 435/176 |
| 4,537,790 | 8/1985 | Horodniceana et al. | 435/180 X |
| 4,539,294 | 9/1985 | Metcalfe et al. | 435/177 X |
| 4,547,463 | 10/1985 | Sakata et al. | 435/180 |
| 4,551,482 | 11/1985 | Tschang et al. | 435/180 X |
| 4,603,111 | 7/1986 | Keller et al. | 435/182 |
| 4,629,742 | 12/1986 | Brady et al. | 521/55 |
| 4,985,468 | 1/1991 | Elmes et al. | 521/63 |

FOREIGN PATENT DOCUMENTS

| | | | |
|---|---|---|---|
| 0060138 | 9/1982 | European Pat. Off. | |
| 0112597 | 7/1984 | European Pat. Off. | 435/180 |
| 3237341 | 10/1982 | Fed. Rep. of Germany. | |
| 8702704 | 5/1987 | World Int. Prop. O. | |

OTHER PUBLICATIONS

Chemical Engineering Science (vol. 40, No. 8, pp. 1321-1354, 85: Karel et al.).
Enzyme Microb. Technol. (vol. 9, Dec. 1987, Turker and Mavituna).
Manny Ratafia, "Issues in Mammalian Cell Culture Production", Pharmaceutical Technology, Nov. 1987.

Primary Examiner—David M. Naff
Attorney, Agent, or Firm—Cushman, Darby & Cushman

[57] ABSTRACT

A porous polymeric support for biological cells is prepared having a total pore volume of at least 75% formed by a plurality of voids having an average diameter within a range of from 1 and 150 μm interconnected by holes. The support is prepared by forming an emulsion containing monomers and/or prepolymers in a continuous phase and having an internal phase that forms the voids of the support, and polymerizing the monomers and/or prepolymers in the continuous phase. The emulsion may be a water-in-oil emulsion with the monomers and/or prepolymers in the oil. Biological cells are introduced into at least the voids of the support. Preferably, the voids have an average size 3 to 15 times the cell size and the holes have an average size 1 to 8 times the cell size. A compound may be produced by passing reactants into the voids via the interconnecting holes to contact the cells in the voids to cause the cells to produce the compound.

19 Claims, No Drawings

POROUS POLYMERIC SUPPORT CONTAINING BIOLOGICAL CELLS IN INTERCONNECTED VOIDS

BACKGROUND OF THE INVENTION

1. Field of the Invention

The present invention relates to a process for preparing a biologically active system comprising biological cells and a solid support therefor, to a system so prepared and to the use of such a system.

In this specification, we use the term "biological cell" broadly, to include for example bacteria, fungi, spores derived therefrom and cells derived from multicellular organisms.

2. Description of the Prior Art

Biologically active systems are known in which a biological organism and/or an active material derived from a biological organism acts as a means by which a chemical reaction, usually a relatively specific reaction, is promoted or performed. Such an organism may be known as a biocatalyst. Such a biological organism or its derivative is thus an integral part of the reaction. Usually moreover the biological material has been especially selected for the particular role it has to play. Its selection and any subsequent purification can be costly and time consuming. The biological material can thus be expensive and valuable. It can therefore be important that it is both used efficiently during any reaction and is not inadvertently lost during or after the reaction.

Supports for enzymes are well known.

U.S. Pat. No. 4,629,742 describes a biologically active system in which a lipase enzyme is immobilised by adsorption on a microporous synthetic thermoplastic hydrophobic polymer. The polymer has a cellular structure, with voids (cells) interconnected by holes, and is typically the material sold under the trade mark Accurel (of Enka, The Netherlands). Accurel is made by cooling a solution of the polymer. The immobilized lipase is used for hydrolysis of liquid fats. The same kind of porous polymer is used in the process of U.S. Pat. No. 4,539,294, in which proteins, e.g. enzymes, are immobilized after first soaking the support with a dilute long-chain cationic solution.

U.S. Pat. No. 4,551,482 also discloses immobilization of an enzyme on a support. In this case the support is hydrophilic macroporous beads. Polystyrene is sulphonated and then charged with polyethyleneimine. The enzyme is said to be ionically bound to the carrier. The support may be formed by suspension polymerization of, for example, styrene and divinylbenzene, with water as the external (continuous) phase. A pore-forming agent. e.g. alkanes, are used to produce the porosity. Alternatively block polymerization is employed, followed by comminution.

An example of chemical bonding of an enzyme to a carrier is to be found in EP-A-147914, where the carrier is controlled pore glass or paper.

It is well known to trap cells within polymer gels. These are formed with the cells present.

The immobilization of biological cells on preformed solid porous support materials appears to be less well-described. In a review in Chemical Engineering Science Vol. 40, No. 8, pp 1321-1354, 1985, Karel et. al. described entrapment of cells in preformed porous matrices. The examples of matrices given are all inorganic.

Use of a porous polyurethane foam, with a large pore size of 2.54 mm, for entrapment of a fungus is described in for example Enzyme Microb. Technol. 1987, vol. 9, December by Turker and Mavituna. WO 87/02704 describes a process wherein the cells are held in cavities between microparticles which are bonded at points of contact to construct a rigid matrix, after the cells have been mixed with the particles. The cells are thus mechanically trapped in the voids of the matrix.

SUMMARY OF THE INVENTION

The present invention has as its object to provide a process for preparing a biologically active system comprising biological cells and a support therefor which in use can allow the desired chemical reaction to take place efficiently and can reduce the loss of cells as a result of the reaction. In addition the system should be easy to form.

The invention provides a process for preparing a biologically active system comprising biological cells and a solid support therefor, which is characterized by preparing as said support a porous polymeric material having a total pore volume of at least 75% and comprising a plurality of interconnected voids having an average diameter within the range of from 1 to 150 $\mu$m and introducing biological cells into at least the voids of the porous polymeric material, wherein the porous polymeric material is made by preparing an emulsion containing monomers and/or prepolymers for the polymeric material and polymerising said monomers and/or prepolymers so as to form the said porous polymeric material.

The cells can be retained on the support material by a variety of physical and/or chemical means e.g. adsorption, entrapment, ionic linking, chemical covalent bonding. The cells are in practice found to be immobilized at least within the voids of the material. In use of the system for production of a compound or compounds, precursors for the compound(s) can pass into the voids for contact with the cells. In, for example, a continuous or semi-continuous process precursors can thus pass through the porous material by passing through the voids containing the immobilized cells.

Some porous materials suitable for use in the present invention are described in for example EP-A-0060138 and can be made by means of the high internal phase emulsion technique described in EP-A-0060138. The porous materials described in EP-A-0060138 are polymeric materials based on polyvinyl materials such as polystyrene.

The use of the cell supports of the invention can provide a number of advantages. The high porosity, compared for example to conventional polystyrene supports, can allow ready passage of reactants into and out of the voids containing the cells. The use of cells can thus take place more efficiently. When used as part of a continuous process a higher through-put rate can thus be achieved. A low pressure drop across a packed bed can also be achieved.

The size of the voids in the porous polymeric materials used in the invention can moreover be particularly appropriate for use with cells. The combination of high porosity and small void size provide moreover a high total surface area per unit volume for support for cells and hence a greater degree of efficiency per unit volume of support. The requirements specified by the invention for void size and porosity can provide an overall surface area of the order of 2 to 100 m$^2$ g$^{-1}$.

In particular, use of the process described in EP-A-60138 to make the polymeric support material can allow the size of the voids and pores to be tailored to individual requirements. In order to vary the void and pore size the aqueous phase in a water-in-oil emulsion suitably has an ionic strength selected to be at least $10^{-4}$ molar, more suitably an ionic strength within the range from $10^{-3}$ to 5 molar. Electrolyte to vary the ionic strength is preferably selected from soluble halides and sulphates. Thus a combination of use of electrolyte and degree of sheer exerted on the emulsion (e.g. by stirring) can be employed to provide a porous polymeric material of predetermined porosity. Further details can be found in European patent application no. 88306447.9 (corresponding to U.S. patent application Ser. No. 07/219,231 filed July 15, 1988, now abandoned) whose contents are hereby incorporated by reference.

The actual void size and porosity selected for any one application can be selected as appropriate. Preferred void sizes lie however within selected size bands within the range 1 to 150 μm and preferred porosity within the range 90 to 98%. In the present process the void and pore size can be selected according to the size and type of the cells that are to be introduced. In particular the void and pore size can be selected to allow ready penetration of the cells into the porous polymeric material and to prevent blockage of the voids and pores by the cells.

Defining the cell size as the average maximum dimension of the biological cells, it is preferred in the invention that the average size of the voids in the polymer material used in the invention is between 3 and 15 times the cell size, more preferably between 6 and 12 times. Likewise the average size of the holes interconnecting the voids is preferably 1 to 8 times the average cell size, more preferably 3 to 6 times.

Since there are no closed voids in the polymer, and since the voids are fully interconnected by holes of controlled size, the biological cells are able to enter all the voids easily, so that a high loading of the polymer support can be achieved and entry of the cells into the polymer is easily achieved. Indeed, it is possible to introduce the cells into the support passively, e.g. by merely shaking the particulate support in a suspension of cells. In these respects, the polymer support formed in the process of the invention has been found superior to the material 'Accurel' mentioned above as an enzyme support.

Instead of passive introduction of cells, the cells may be introduced into the support by passing a cell suspension through a packed bed constituted by the support.

Another advantage of the polymer material used as the support in the present invention is that, when cross-linked, it can be sterilized by heat, e.g. by autoclaving, which is not possible with a thermoplastic material such as Accurel.

The interconnected structure of the porous polymeric support materials used in the invention can provide a low resistance to fluid flow through the support material allowing good flow rates at low pressure drops. If desired, viscous liquids, e.g. oils, can be passed through the system. The porous support materials used in the invention have additionally been observed to have beneficial release properties. Such a property can be especially advantageous in a reaction in which gas is released as product which has to escape from the system in order to ensure that surface area is available for the reaction to continue. It seems that the void size and interconnecting nature of the voids can allow ready removal of a gaseous product from the system.

The readily accessible surface area and high porosity can be particularly appropriate for rapid cell reaction kinetics and moreover can circumvent some of the mass-transfer limitations met in the use of gel and small pore materials.

The porous materials used in the invention can be available in a wide variety of shapes. The shapes and forms can be provided by machining or during preparation e.g. by moulding or castingin e.g. block, sheet, membrane, tubular or more complex geometric shapes. Alternatively the material can be provided in particulate form and packed into a reactor of any desired shape.

The use of block form can however be particularly advantageous as it allows ready and quick loading of one or more integral blocks of the porous material into a reactor. The blocks can be ready loaded with the required cells and can thus permit a quick interchange in a reactor between the same or different cell systems, or the blocks can be loaded in situ with cells. In either case however the use of block form avoids both the need to pack a reactor with particles and any of the well-known problems such as channelling that can occur with particle packed reactors.

Desirable mechanical properties of the porous material can include high incompressibility and flexibility. The provision of support material of relatively high incompressibility can be particularly important, since it can allow the provision of biologically active systems and processes on a industrial scale e.g. reactors in the range of from 1 to 5 m$^3$ capacity. A number of conventional materials used satisfactorily on a laboratory scale are unsuitable for use on a large scale due to their lack of compressive strength e.g. naturally occurring organic polymers.

Further details concerning suitable porous materials for use in the present invention can be found in the above mentioned EP-A-60138 and additionally in EP-A-105634, EP-A-156541, EP-A-157504, GB-A-2155481, EP-A-200528 and EP-A-223574 and pending patent applications EP-A-239360, EP-A-240342, EP-A-264268, EP-A-289238, EP-A-288310 and European patent application no. 88306447.9 mentioned above. Each of these patent specifications describes a porous material which conforms to the present porosity requirements. In all cases the material can be made by polymerising starting materials in the form of a high internal phase emulsion which can either be a water-in-oil emulsion, an oil-in-water emulsion or an emulsion formed between any two sufficiently immiscible solutions. By "water" we mean aqueous bases and by "oil" we mean immiscible with aqueous systems. The materials described in the different specifications differ in their starting materials and/or end properties. All of the just mentioned patent specifications are hereby incorporated by reference.

The biological cells used in the present invention can be selected from the group comprising microbes, yeast cells, fungi, animal cells, plant cells and mixtures thereof. In some instances the cells have been found to adsorb directly onto the surface of the porous material, but in other cases it may be necessary to provide a chemical linkage to bind the cells. In such cases porous materials from the above mentioned patent specifications whose surfaces have been chemically modified have been found appropriate to provide chemical binding sites for the cells. Whatever method of attachment of the cells is employed, the use of the present materials have been found particularly appropriate as the cells can be immobilised within the interconnecting voids providing some or all of the advantages mentioned above.

A particular advantage found is that cells can adapt their morphology to create strong bonds to the polymeric support. Thus there may be initially only a loose interaction with the support. This initial interaction may be a process of physical adsorption at the polymer surface, i.e. without covalent bonding and without ionic bonding. Subsequently the cells may become chemically attached by adaption of the cells themselves.

Cells may be immobilised on the support in the invention together with other biological material, in particular an enzyme.

Within the invention, cells may be grown in situ in the polymeric support. It is advantageous to introduce the cells into the support while the cells are in a growth-promoting medium.

Use of the biologically active systems of the present invention can be made in a wide variety of industries including for example food and drink, and pharmaceuticals and fine chemicals. The present system can be operated in a range of media, both aqueous and non-aqueous. Examples of particular applications of micro-organisms immobilised in aqueous media include the continuous production of alcohol from sugars and of wine from grape concentrates, the removal of glucose from product streams and the selective reduction of perfume materials. Processes of use of the systems of the invention include bio-catalysis and other processes such as cell growth, extraction of metals from solution, etc.

EXAMPLES

Embodiments of the present invention will now be described by way of example only with reference to the following Examples.

EXAMPLE 1

Experiments were performed using a polymeric porous support material prepared in accordance with the procedures described in EP-A-0060138. The material was thus a porous polyvinyl based material. The experiments used Saccharomyces yeast cells which were immobilised on the support material. The system thereby obtained was successfully used for the continuous production of alcohol in a packed bed reactor. The volume efficiency of the reactor was found to be very good.

The structure of the polymer, in particular the size of the voids and the size of the interconnecting holes, was specifically selected having regard to the diameter of the yeast cells employed, which reached a maximum size of approximately 8 μm in free culture, but were of the order of 5 μm. A suitable combination of void and hole size was assessed to be approximately 45 μm and 15 μm respectively, to allow full penetration of the porous material and to prevent void blockage by adhesion of cells to the polymer walls.

Preparation of the support material was as follows. First there was formed 1 liter of high internal phase emulsion in which the oil phase, which made up 10% of the volume, contained styrene, divinyl benzene and Span 80 (a widely available surfactant) in the ratios 10:1:2, and the aqueous phase contained potassium persulphate at a concentration of 2.5 g liter and calcium chloride ($10^{-4}$M). The latter was included as a co-regulator of the final void and pore size. The emulsion was subjected to relatively homogeneous post-formation sheer and was then kept at 60° C. for 10 hours to allow polymerisation to occur. The resulting polymeric material was comminuted into particles, sieved to collect the 425 μm to 1400 μm size fraction, washed free of surfactant and salt using continuous flow hot isopropyl alcohol followed by deionised water and finally dried. Analysis of samples by scanning electron microscopy revealed the required combination of void and hole size i.e. 45 μm and 15 μm respectively. Total pore volume is about 90%.

For cell immobilization, portions of polymer were first placed in quarter Ringers solution and autoclaved at 120° C., 15 lb/in² pressure (105 kPa), for 20 mins to sterilize them. Excess quarter Ringers solution was decanted off and the polymeric material resuspended in approximately ten times its volume of Sabourands dextrose broth, which was subsequently innoculated with a commercial wine yeast Saccharomyces cerevisiae. The innoculated flasks were incubated with shaking at room temperature for approximately 5 days, with a fresh media change being made on alternate days. After incubation the contents of all flasks were pooled in a 2 liter sterile flask and the supernatant discarded. Approximately one liter of sterile 0.1% peptone water with 2% Tween 80 (surfactant) was added to the flask and the contents rigorously shaken, in order to facilitate the removal of loosely adhering yeast while not detaching the firmly immobilized cells. This procedure was repeated 8 times, with every second washing including centrifugation of the slurry at 3,000 RPM for 20 minutes and discarding of the supernatant.

After the final centrifugation the packed slurry of particles was resuspended in sterile quarter Ringers solution and a sample removed for scanning electron microscopy analysis. Air-dried particles of polymeric material were observed to have large numbers of cells attached to the polymeric wall surface; in many cases evidence of attachment via extracellular material was observed.

In order to test the activity of the cells immobilized on the porous polymeric material the slurry was packed firmly into a column of length 465 mm and diameter 13 mm, to form a packed-bed reactor, which was then incorporated into a through-flow system having gas inlet and outlet systems, a feed tank, a pump and a pressure sensor. A 15% sucrose solution containing essential minerals for cell function was pumped into the reactor for a single-pass conversion of sugar to alcohol.

The alcohol production data is summarised in the following Table.

TABLE

| | |
|---|---|
| Fermentation type | Continuous flow, single pass |
| Feed stock | 15% sucrose + minerals |
| Temperature | 20° C. |
| Yeast | Standard wine yeast (Saccharomyces cerevisiae) |
| Final alcohol concentration (g/dl) | 6–10.5 |
| Volume efficiency of reactor Kg EtOH/m³/h | 9–18.0 |

The reactor was allowed to run continuously for a period of 22 days, the figures given in the Table being minima and maxima for that period. Sugar conversion was found to be in excess of 98%, but not all the sugar was converted to ethanol. It is presumed that some of the sugar was metabolized by the cells for growth and reproduction. However, the volume efficiency of the system run at the relatively low temperature of 20° C. with a standard wine yeast was excellent.

A significant observation was the gas-transfer properties observed. Although carbon dioxide was continually released during fermentation, the gas was not apparent within the main body of the column, where pocketing and bed lifting were entirely absent and gas release was only observed at the top surface of the bed. Such gas release properties suggest that porous polymeric material acts to channel released gas preferentially through the voids and holes of adjacent particles, a particularly advantageous property for any packed bed system requiring gas release or influx.

Analysis of the polymer particles by electron microscopy techniques after the alcohol production indicated dense covering of the walls of the polymeric material throughout the particles and in some cases, small flocs (cell aggregates) were observed within voids. A further significant observation was that the cells showed an altered morphology, being less rounded, more moulded to the polymer surface and adjacent cells appeared to be attached to each other. Thus the cells appeared to adopt favourable sites and morphology, demonstrating the suitability of the present porous polymeric material for yeast cell immobilization.

EXAMPLE 2

Following procedures essentially as in Example 1, Winecraft Blend No 4 grape juice concentrate (ex Home Winecraft, Wigston, Leicester, UK) was pumped into the column instead of 15% sucrose. 5 liters of palatable wine containing 10% w/v alcohol were produced in five days in a continuous operation. For comparison, a batch sample was prepared over 28 days by conventional home-brew procedures. This batch product and the continuous fermentation product of this Example were analysed using gas chromatographic and other techniques. The composition of the samples was almost identical, apart from the slightly higher alcohol content of the batch sample. Such evidence indicates that the immobilized yeast cells in the system of the invention do not exhibit altered or abnormal metabolism as might otherwise be expected under stress situations leading to undesirable metabolic excretion products.

EXAMPLE 3

Animal cells such as hybridoma cells are of particular interest in the preparation of monoclonal antibodies. Many eukaryotic cell types in culture are 'anchorage dependent' i.e. in addition to the normal requirements of readily accessible nutrients and protection from abrasion damage, they require a suitable support for adhesion and growth. These supports allow the establishment of cells and regulate cell behavior (morphology, mobility, growth and metabolism). A porous polymeric material in accordance with the invention in particulate form with the desired combination of void size, hole diameter and surface chemical characteristics, was employed successfully in a series of experiments involving the culturing of anchorage-dependent rat embryo fibroblasts (REF). The porous polymeric material employed had an average void size of 90 $\mu$m and an average pore size of 30 $\mu$m and was appropriate to permit inter-void penetration of cells and full 'spread' morphology.

Preparation of the material began with the formation of a high internal phase emulsion as in Example 1, except that in the present case the aqueous phase was 1.0M in calcium chloride. This ionic strength coupled with a post-formation sheer time of approximately 2 minutes provided a material having the required combination of void and pore sizes.

Following polymerisation, comminution and washing (as in Example 1), the dried material was treated by submersion in 98% sulphuric acid for 30 mins, followed by neutralisation with 1N sodium hydroxide and finally by washing with de-ionised water and then drying in order to render the surface hydrophilic, i.e. suitable for the cell adhesion in this instance. Initially, the cell binding may be ionic.

For cell growth studies, 30 to 40 particles of autoclaved polymer were mixed with 1 to 2 mls of rat embryo fibroblast (REF) suspended in Dulbecco's Modified Eagles Medium (DMEM), supplemented with 10% foetal calf serum, L-glutamine and penicillin/streptomycin. Cultures were maintained for 6 hours at 37° C. under a 5% $CO_2$ atmosphere.

Adhesion and growth of the REF cells on and within the porous polymer were examined by both scanning (SEM) and transmission electron microscopy (TEM) using conventional techniques. Healthy anchorage-dependent cells in culture normally exhibit good 'spread' morphology and have characteristic well-developed cytoskeletal features. The surfaces of the porous polymer were found to be well covered in 'spread' cells, and in many cases cells were actually seen to bridge voids within the polymer network, further establishing the suitability of the material for cell growth and adhesion. TEM analysis of cell ultrastructure indicated the presence of highly specialised cell membrane/polymer attachment points as well as the normal cytoskeletal structures such as bundles of actomyosin filaments terminating at focal adhesions, and well established 10 nm filament and microtublar systems. Thus the healthy morphology and ultrastructural features of the (REF) cells indicated that the void and pore sizes of the present porous polymeric material were suitably selected for the culturing of anchorage-dependant animal cells.

EXAMPLE 4

Following the procedure as described in Example 3, a system was produced in which the REF cells were substituted by anchorage-dependent baby hamster kidney cells (BHK). The BHK cells showed good 'spread' morphology, made specialised cell-support adhesion plaques and exhibited a normal cytoskeletal system. These features, typical of normal cell function in culture, provide evidence for the usefulness of the present porous polymeric material as a support material for animal cells.

EXAMPLE 5

To allow for penetration and growth of fungal hyphae, a polyvinyl polymeric material was prepared having a porosity and void size appropriate for the organism.

Porous support preparation: First there was formed a high internal phase water-in-oil emulsion in which the oil phase comprised styrene, divinylbenzene and Span 80 (4.42, 0.44 and 0.88 kg respectively) and the aqueous phase contained water, sodium persulphate and calcium chloride (44.25, 0.097 and 9.0 kg respectively). The emulsion was subjected to 30 minutes post formation sheer at 85 rpm. Polymerisation was subsequently carried out at 60° C. over 40 hours. The blocks of resulting polymer was cut into slices 0.5 cm thick, from which discs 85 mm in diameter were cut. The polymer was subsequently washed as in Example 1. Microscope examination of the material indicated that the material had a porosity of 90%, a void size of at least 30 μm, and an interconnecting hole size of at least 10 μm.

Under aseptic conditions, a cleaned and autoclaved polymeric disc was filled with Sabourands dextrose broth, placed in a petri dish and the upper surface coated with *Aspergillus niger* inoculum. Innoculated plates were incubated at 28° C. until dense fungal growth was observed, after which the polymeric disc with associated immobilized fungus was soaked in absolute ethanol and then air dried. Sections through the disc were taken and analysed by scanning electron microscopy. Results indicated dense hyphal penetration of the porous polymeric network, and extending from the hyphae and polymeric surface were numerous spore forming bodies rich in spores. Thus, the present porous polymeric material was capable of providing suitable support and nutrient supply for fungal growth and reproductive development, in combination with good solid protection for the fragile hyphae.

What is claimed is:

1. A process of preparing a compound comprising:
   (a) providing a biologically active system comprising biological cells and a solid support therefor, said support being formed of porous polyvinyl polymeric material having a porosity comprising voids and holes interconnecting said voids, said biologically active system being prepared by a process including the steps of:
      (i) preparing an emulsion having a continuous phase and an internal phase containing vinyl monomers and/or prepolymers, in which emulsion said monomers and/or prepolymers are present in the continuous phase of the emulsion, and said voids of said polymeric material being formed by the internal phase of the emulsion,
      (ii) polymerising said monomers and/or prepolymers in said continuous phase of said emulsion so as to form said polymeric material as a porous material having a total pore volume of at least 75% and having said porosity comprising said voids and holes, said voids having an average diameter within the range of from 1 to 150 μm,
      (iii) introducing biological cells into at least said voids of said polymeric material, said biological cells having a cell size such that the average size of said voids in said polymeric material is in the range 3 to 15 times said cell size of the biological cells, and the average size of said holes in said polymeric material is in the range 1 to 8 times the cell size of the biological cells, and
   (b) passing reactants into said voids via said interconnecting holes so as to contact said cells with said reactants, thereby causing said cells to produce said compound.

2. A process for preparing a biologically active system comprising biological cells and a solid support therefor, said support being formed of porous polyvinyl polymeric material having a porosity comprising voids and holes interconnecting said voids, said process including the steps of:
   (i) preparing an emulsion having a continuous phase and an internal phase containing vinyl monomers and/or prepolymers, in which emulsion said monomers and/or prepolymers are present in the continuous phase of the emulsion, and said voids of said polymeric material being formed by the internal phase of the emulsion,
   (ii) polymerising said monomers and/or prepolymers in said continuous phase of said emulsion so as to form said polymeric material as a porous material having a total pore volume of at least 75% and having said porosity comprising said voids and holes, said voids having an average diameter within the range of from 1 to 150 μm, and
   (iii) introducing biological cells into at least said voids of said polymeric material, said biological cells having a cell size such that the average size of said voids in said polymeric material is in the range 3 to 15 times said cell size of the biological cells, and the average size of said holes in said polymeric material is in the range 1 to 8 times the cell size of the biological cells.

3. A process according to claim 2 wherein the emulsion is a water-in-oil emulsion having an aqueous phase and an oil phase, the monomers and/or prepolymers being in the oil phase.

4. A process according to claim 3 wherein the aqueous phase has an ionic strength of at least $10^{-4}$ molar electrolyte.

5. A process according to claim 4 wherein the ionic strength of the aqueous phase is in the range from $10^{-3}$ to 5 molar electrolyte.

6. A process according to claim 4 wherein the electrolyte is selected from the group comprising soluble halides and sulphates.

7. A process according to claim 2 including the step of washing the formed porous polymeric material prior to introducing the cells.

8. A process according to claim 2 wherein the polymeric porous material formed has a total pore volume of at least 90%.

9. A process according to claim 2 wherein the polymeric material is a cross-linked polymer.

10. A process according to claim 2 wherein on initial contact with the support the cells become localized within the support without covalent bonding.

11. A process according to claim 10 wherein on initial contact with the support the cells become localized within the support without either covalent or ionic bonding.

12. A process according to claim 2 wherein the cells become chemically bound to the material.

13. A process according to claim 2 wherein the cells are introduced into the support while in a growth-promoting medium.

14. A process according to claim 2 wherein the cells are selected from the group consisting of yeast cells, fungi, animal cells, plants cells and mixtures thereof.

15. A process according to claim 2 wherein the average size of said voids in the porous polymer material is in the range 6 to 12 times the cell size of the biological cells.

16. A process according to claim 2 wherein the average size of the holes is in the range 3 to 6 times the cell size.

17. A biologically active system prepared by a process according to claim 2.

18. A process for preparing a biologically active system comprising biological cells and a solid support for the cells, comprising the steps of preparing said support as a porous polyvinyl polymeric material having a porosity comprising voids and holes interconnecting said voids, said process including the steps of:

(i) preparing an emulsion having a continuous phase and an internal phase containing vinyl monomers and/or prepolymers, in which emulsion said monomers and/or prepolymers are present in the continuous phase of the emulsion and the internal phase of the emulsion is at least 75% by volume, (ii) polymerising said monomers and/or prepolymers in said continuous phase of said emulsion so as to form said porous polymeric material as a material having a total pore volume of at least 75% and having said porosity comprising said voids and said holes, said voids being represented by the internal phase of the emulsion and having an average diameter within the range of from 1 to 150 μm, and (iii) thereafter introducing biological cells into a least said voids of said polymeric material while the cells are in a growth-promoting medium so that the cells initially become localized within the support without covalent bonding and subsequently adapt their morphology to form binding linkages to the support, said biological cells having a cell size such that the average size of said voids in said polymeric material is in the range 3 to 15 times said cell size of the biological cells, and the average size of said holes in said polymeric material is in the range 1 to 8 times the cell size of the biological cells.

19. A biologically active system prepared by a process according to claim 18.

* * * * *